(12) United States Patent
Goto et al.

(10) Patent No.: US 10,036,082 B2
(45) Date of Patent: Jul. 31, 2018

(54) ZIRCONIUM EXTRACTANT AND METHOD FOR EXTRACTING ZIRCONIUM

(71) Applicants: Kyushu University, National University Corporation, Fukuoka-shi (JP); SUMITOMO METAL MINING CO., LTD., Tokyo (JP)

(72) Inventors: Masahiro Goto, Fukuoka (JP); Fukiko Kubota, Fukuoka (JP); Yuzo Baba, Fukuoka (JP)

(73) Assignees: Kyushu University, National University Corporation, Fukuoka-shi (JP); SUMITOMO METAL MINING CO., LTD., Tokyo (JP)

( * ) Notice: Subject to any disclaimer, the term of this patent is extended or adjusted under 35 U.S.C. 154(b) by 0 days.

(21) Appl. No.: 15/544,079

(22) PCT Filed: Sep. 28, 2015

(86) PCT No.: PCT/JP2015/077355
§ 371 (c)(1),
(2) Date: Jul. 17, 2017

(87) PCT Pub. No.: WO2016/117175
PCT Pub. Date: Jul. 28, 2016

(65) Prior Publication Data
US 2018/0010211 A1  Jan. 11, 2018

(30) Foreign Application Priority Data

Jan. 20, 2015 (JP) .................................. 2015-008636

(51) Int. Cl.
| | | |
|---|---|---|
| C22B 34/00 | (2006.01) | |
| C22B 34/14 | (2006.01) | |
| C07C 237/06 | (2006.01) | |
| B01D 11/04 | (2006.01) | |

(52) U.S. Cl.
CPC ............ C22B 34/14 (2013.01); C07C 237/06 (2013.01); B01D 11/0492 (2013.01)

(58) Field of Classification Search
CPC ..... C22B 3/0024; C22B 34/14; C07C 237/06; B01D 11/04; B01D 11/0492
USPC ............................................ 423/70; 252/184
See application file for complete search history.

(56) References Cited

U.S. PATENT DOCUMENTS

| | | | |
|---|---|---|---|
| 5,223,232 A | 6/1993 | Cuillerdier et al. | |
| 5,250,517 A | 10/1993 | Branca et al. | |
| 6,267,936 B1 | 7/2001 | Delmas et al. | |
| 6,709,641 B1 | 3/2004 | Gutknecht et al. | |
| 8,951,486 B2 * | 2/2015 | Goto ................... | C22B 3/0005 423/21.1 |
| 9,011,804 B2 * | 4/2015 | Goto ................... | C22B 3/0005 423/150.1 |
| 9,458,526 B2 | 10/2016 | Goto et al. | |
| 9,803,262 B2 * | 10/2017 | Goto ................... | C22B 58/00 |
| 2005/0124765 A1 | 6/2005 | Seko | |
| 2007/0248514 A1 | 10/2007 | Cheng et al. | |
| 2013/0102806 A1 | 4/2013 | Sakaki et al. | |
| 2014/0234187 A1 | 8/2014 | Goto | |
| 2014/0328737 A1 | 11/2014 | Goto et al. | |
| 2015/0315674 A1 | 11/2015 | Goto et al. | |

FOREIGN PATENT DOCUMENTS

| | | |
|---|---|---|
| AU | 725800 B2 | 10/2000 |
| CA | 2827601 * | 5/2013 |
| CN | 101519427 A | 9/2009 |
| CN | 103582711 A | 2/2014 |
| CN | 104822851 A | 8/2015 |
| EP | 0834581 A1 | 4/1998 |
| EP | 2679693 A1 | 1/2014 |
| EP | 2682486 A1 | 1/2014 |
| EP | 2712940 A1 | 4/2014 |
| JP | H04-074711 A | 3/1992 |
| JP | 05-070856 A | 3/1993 |
| JP | H06-200336 A | 7/1994 |
| JP | H09-143589 A | 6/1997 |
| JP | H09291320 A | 11/1997 |
| JP | 2000-212658 A | 8/2000 |
| JP | 2000-234130 A | 8/2000 |
| JP | 2000-313928 A | 11/2000 |
| JP | 2002-539324 A | 11/2002 |
| JP | 2007327085 A | 12/2007 |
| JP | 2009-256291 A | 11/2009 |
| JP | 2010-174366 A | 8/2010 |
| JP | 2012-102062 A | 5/2012 |
| JP | 2013-057115 A | 3/2013 |
| JP | 2013-216656 A | 10/2013 |
| WO | 2005/073415 A1 | 8/2005 |
| WO | 2012/005183 A1 | 1/2012 |
| WO | 2013/069562 A1 | 5/2013 |
| WO | 2013/069563 * | 5/2013 |
| WO | 2013069562 A1 | 5/2013 |
| WO | 2013069563 A1 | 5/2013 |
| WO | 2013/136941 A1 | 9/2013 |
| WO | 2014/148431 A1 | 9/2014 |

OTHER PUBLICATIONS

Kubota et al, "Extraction behavior of rare earth ions . . . " Kidorui, vol. 64, pp. 44-45, 2014.*

(Continued)

*Primary Examiner* — Steven J Bos
(74) *Attorney, Agent, or Firm* — Locke Lord LLP; James E. Armstrong, IV; Nicholas J. DiCeglie, Jr.

(57) ABSTRACT

Provided are: an extractant which is capable of quickly and highly efficiently extracting zirconium from an acidic solution that is obtained by acid leaching a material containing zirconium and scandium such as an SOFC electrode material; and a method for extracting zirconium, which uses this extractant. A zirconium extractant according to the present invention is composed of an amide derivative represented by general formula (I). In the formula, R1 and R2 respectively represent the same or different alkyl groups, each of which may be linear or branched; R3 represents a hydrogen atom or an alkyl group; and R4 represents a hydrogen atom or an arbitrary group other than an amino group, said arbitrary group being bonded, as an amino acid, to the α carbon.

6 Claims, 3 Drawing Sheets

(56) References Cited

OTHER PUBLICATIONS

Pajewski et al, "The effect of midpolar regime . . ." New Journal of Chemicstry, 2007, 31, pp. 1960-1972.*

Baba et al, "Development of novel extractants . . ." Ind. and Engineering Chemistry Research, 53, pp. 812-816, Dec. 25, 2014.*

International Search Report dated Oct. 27, 2015, issued for PCT/JP2015/077355.

Office Action for U.S. Appl. No. 14/650,364, dated Feb. 17, 2017.

Bourget C et al: "CYANEX® 301 binary extractant systems in cobalt/nickel recovery from acidic sulphate solutions", Hydrometallurgy, Elsevier Scientific Publishing CY. Amsterdam, NL, vol. 77, No. 3-4, Jun. 1, 2005 (Jun. 1, 2005), pp. 203-218, XP027652523.

J.M. Zhao et al: "Synergistic extraction and separation of valuable metals from waste cathodic material of lithium ion batteries using Cyanex272 and PC-88A", Separation and Purification Technology, vol. 78, No. 3, Apr. 1, 2011 (Apr. 1, 2011), pp. 345-351, XP055013869.

Extended European search report for European Patent Application No. 13862883.9, dated Nov. 20, 2015.

International Search Report for International Application No. PCT/JP2013/074158, dated Nov. 26, 2013.

Kunitake, et al., "Regulation of catalytic . . . membranes" Studies in Organic Chemistry, 1983, 13 (Biomimetic Chem.), pp. 147-162.

Office Action for U.S. Appl. No. 14/423,061 dated Mar. 13, 2017.

K. Shimojo, H. Naganawa, J. Noro, F. Kubota and M Goto; Extraction behavior and separation of lanthanides with a diglycol amic acid derivative and a nitrogen-donor ligand; Anal. Sci., 23, 1427-30, Dec. 2007.

Office Action for JP Application No. 2013-084951, dated Jan. 14, 2014.

CAS Registration No. 1156229-80-9.

EESR for EP Application No. 12848105.8, dated Jan. 22, 2014.

Naganawa H, et al: "A New Green Extractant of the Diglycol Amic Acid Type for Lanthanides", Solvent Extraction Research and Development, Japan, Japanese Association of Solvent Extraction, Saga, JP, vol. 14, Jan. 1, 2007 (Jan. 1, 2007), pp. 151-159, XP002597763, ISSN: 1341-7215 p. 152.

Singh D K et al: "Extraction of rare earths and yttrium with high molecular weight carboxylic acids", Hydrometallurgy, Elsevier Scientific Publishing CY. Amsterdam, NL, vol. 81, No. 3-4, Mar. 1, 2006 (Mar. 1, 2006), pp. 174-181, XP027884077, ISSN: 0304-386X, [retrieved on Mar. 1, 2006] p. 174.

EESR for EP Application No. 12847107.5, dated Feb. 6, 2014.

Holger Stephan et al: "Liquid-Liquid Extraction of Metal Ions with Amido Podands", Solvent Extraction and Ion Exchange, Taylor & Francis Group LLC, US, vol. 9, No. 3, Jan. 1, 1991 (Jan. 1, 1991), pp. 459-469, XP008157386, ISSN: 0736-6299, DOI:10.1080/07366299108918064 [retrieved on Mar. 30, 2007] figure 1.

Office Action for JP Application No. 2014-022868, dated Apr. 8, 2014.

CAS Registration No. 1153237-54-7.
CAS Registration No. 1153399-39-3.
CAS Registration No. 1178468-85-3.
CAS Registration No. 1179174-30-1.
CAS Registration No. 1182789-10-1.
CAS Registration No. 1183588-00-2.
CAS Registration No. 1291231-35-0.

EESR for EP Application No. 13761717.1, dated Oct. 14, 2014.

Smith B F et al: "Amides as phase modifiers for N,N'—tetraalkylmalonamide extraction of actinides and lanthanides from nitric acid solutions", Separation Science and Technology, Dekker, New York, NY, US, vol. 32, Jan. 1, 1997 (Jan. 1, 1997), pp. 149-173, XP009180393.

Office Action for U.S. Appl. No. 14/130,283, dated Feb. 26, 2015.

Office Action for CN Application No. 201380002904.1, dated Jun. 26, 2015.

Office Action for CN Application No. 201480008628.4, dated Mar. 10, 2016.

EESR for EP Application No. 14770382.1, dated Feb. 16, 2016.

Office Action for U.S. Appl. No. 14/765,307, dated Apr. 6, 2016.

Office Action for China Patent Application No. 201380042793.7, dated Nov. 23, 2015.

International Search Report of PCT/JP2013/062481, dated Jul. 9, 2013.

Morizono Hirofumi et al., Liquid-liquid extraction of transition metal ions with an alkylhistidine extractant, Separation and Purification Technology, Jul. 29, 2011, vol. 80 No. 2, p. 390-395.

Robert Pajewski, "The effect of midpolar regime mimics on anion transport mediated by amphiphilic heptapeptides", New Journal of Chemistry, 2007, 31, pp. 1960-1972.

Yuzo Baba et al., "Development of Novel Extractants with Amino Acid Structure for Efficient Separation of Nickel and Cobalt from Manganese Ions", Industrial & Engineering Chemistry Research, vol. 53, No. 2, Dec. 25, 2013, pp. 812-818.

\* cited by examiner

13C-NMR SPECTRUM OF SAMPLE

<MEASUREMENT CONDITIONS>
SAMPLE CONCENTRATION: ABOUT 30 wt%/CDCl$_3$ SOLUTION
NUMBER OF SCANS: 1024 SCANS
BASE PEAK: $^{13}$C IN CDCl$_3$ ($\delta$ =76.9ppm)

ZIRCONIUM EXTRACTANT AND METHOD FOR EXTRACTING ZIRCONIUM

TECHNICAL FIELD

The present invention relates to a zirconium extraction agent and a zirconium extraction method.

BACKGROUND ART

Zirconium is used in the form of alloys as a cladding material for fuel rods in a nuclear reactor, and furthermore is a valuable metal used for e.g. a white pigment and a piezoelectric element as oxidized zirconium. In the meantime, scandium with the lowest atomic number among the rare earth elements is used as e.g. a material for metal halide lamps, an additional element in alloys and, in recent years, an additional element in catalytic ceramics.

Furthermore, the use of ScSZ ($Sc_2O_3$-doped $ZrO_2$/Scandia-stabilized zirconia) as an electrolyte for solid oxide fuel cells called SOFC has been recently considered as a use common to both zirconia and scandium.

As described above, both zirconium and scandium are valuable elements and the efficient recovery and purification of them have been attempted. In the future, it is also considered that used SOFCs be recycled to separate, recover and reuse scandium and zirconium.

As a method used for such separation, for example, it is considered that an electrolyte, ScSZ, for the above used SOFCs is dissolved by adding a strong acid, impurities are separated using a means such as neutralization-precipitation, and furthermore scandium and zirconium are separated by a means such as solvent extraction.

Patent Document 1, for example, describes a method for separating iron and/or zirconium from actinide and/or lanthanide existing in an aqueous acid solution by a propanediamide. This method uses a 5-substituted propanediamide having the structure represented by the following chemical formula:

[Chem. 1]

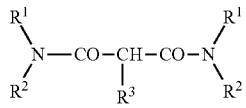

(wherein, $R^1$, $R^2$ and $R^3$, which may be the same or different, are an alkyl group which optionally has one or two oxygen atoms in the chain.)

Patent Document 1 above, however, does not describe the behavior of scandium, which belongs to Group 3 elements together with the lanthanoids but has chemical properties slightly different from each other, and there is not knowledge to separate zirconium and scandium.

For the separation of zirconium and scandium, Patent Document 2 provides a technique for separating $Sc^{3+}$ from an aqueous solution containing $Sc^{3+}$ and metal ions other than $Sc^{3+}$ using a versatile reagent, and particularly discloses carrying out the step of adding an organic solvent and a first chelating agent to form a complex with $Sc^{3+}$ in the organic solvent to an aqueous solution containing $Sc^{3+}$ and metal ions other than $Sc^{3+}$, the step of forming a mixed solution by mixing the aqueous solution and the organic solvent to form a complex of $Sc^{3+}$ and the first chelating agent, and the step of separating the mixed solution into the organic phase and the aqueous phase.

When using the method described in Patent Document 2, however, as shown in the text and FIGS. 1 to 7 in Patent Document 2, for example, scandium is extracted instead of zirconium, or the extraction behaviors of iron and aluminum partially have the same tendency as the extraction behaviors of zirconium, and thus it cannot be said that this is sharp separation, and there is a problem in that it is difficult to obtain high-purity zirconium.

Patent Document 1: Japanese Unexamined Patent Application, Publication No. H05-70856
Patent Document 2: Japanese Unexamined Patent Application, Publication No. 2013-57115

DISCLOSURE OF THE INVENTION

Problems to be Solved by the Invention

An object of the present invention is to provide an extraction agent which can quickly extract zirconium with high efficiency from an acidic solution obtained by acid leaching of a material containing zirconium and scandium such as an SOFC electrode material, and a method for extracting zirconium using this extraction agent.

As a result of repeated diligent research to solve the above problem, the present inventors found that zirconium could be recovered from a solution containing scandium and various kinds of impurities in large amounts by providing a zirconium extraction agent comprising an amide derivative represented by the following general formula (I), thereby completing the present invention.

Means for Solving the Problems

Specifically, the following are provided in the present invention.

(1) The present invention is a zirconium extraction agent comprising an amide derivative represented by the following general formula (I):

[Chem. 2]

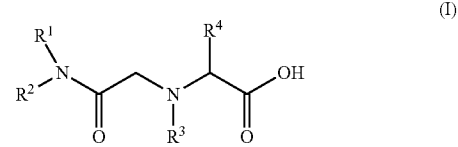

(wherein $R^1$ and $R^2$ each represents the same or different alkyl group,
the alkyl group may be a straight chain or a branched chain,
$R^3$ represents a hydrogen atom or an alkyl group, and
$R^4$ represents a hydrogen atom or any group other than an amino group which is bound to the α carbon as an amino acid).

(2) The present invention is also the zirconium extraction agent described in (1), wherein in the formula, the alkyl group in $R^1$ and $R^2$ is a branched chain, and the number of carbons in the alkyl group in $R^1$ and $R^2$ is 5 or more and 11 or less.

(3) The present invention is also the zirconium extraction agent described in (1) or (2), wherein the amide derivative is any one or more of a glycine amide derivative, a histidine amide derivative, a lysine amide derivative, an aspartic acid amide derivative and a normal-methyl glycine derivative.

(4) The present invention is also a method for extracting zirconium, wherein an acidic solution containing zirconium or an acidic solution containing zirconium and scandium is subjected to solvent extraction using a zirconium extraction agent described in any of (1) to (3) to extract the zirconium from the acidic solution.

(5) The present invention is also the method for extracting zirconium described in any of (1) to (4), wherein the acidic solution further contains one or more selected from scandium, titanium, lanthanum and yttrium, and the acidic solution is subjected to the solvent extraction with the pH of the acidic solution adjusted to 0.8 or lower.

(6) The present invention is also the method for extracting zirconium described in (4) or (5), wherein after solvent extraction using the zirconium extraction agent, an acidic solution with a pH of 0 or higher and 0.5 or lower is mixed with the extraction agent which has extracted the zirconium from the acidic solution to carry out back extraction, and the extraction agent and the acidic solution are then separated to separate zirconium and at least one or more components selected from scandium, titanium, lanthanum and yttrium.

(7) The present invention is also the method for extracting zirconium described in (6), wherein after the back extraction, the pH of the acidic solution is adjusted to 1.0 to separate zirconium or zirconium and scandium, and one or more components selected from titanium, lanthanum and yttrium, and an acidic solution adjusted to a pH of 0.2 or lower is then mixed with the extraction agent to separate zirconium and scandium.

(8) The present invention is also the method for extracting zirconium described in any of (4) to (7), wherein the acidic solution is obtained by acid dissolution of an electrode material for solid oxide fuel cells.

Effects of the Invention

According to the present invention, zirconium can be recovered from an acidic solution containing scandium and various kinds of impurities in large amounts at one time. It is only required to carry out the step of extracting zirconium from an acidic solution once, and the volume of extraction liquid can be significantly reduced. Therefore, compact equipment can be used and zirconium can be quickly extracted with high efficiency from an acidic solution containing zirconium.

PREFERRED MODE FOR CARRYING OUT THE INVENTION

Figure 1:
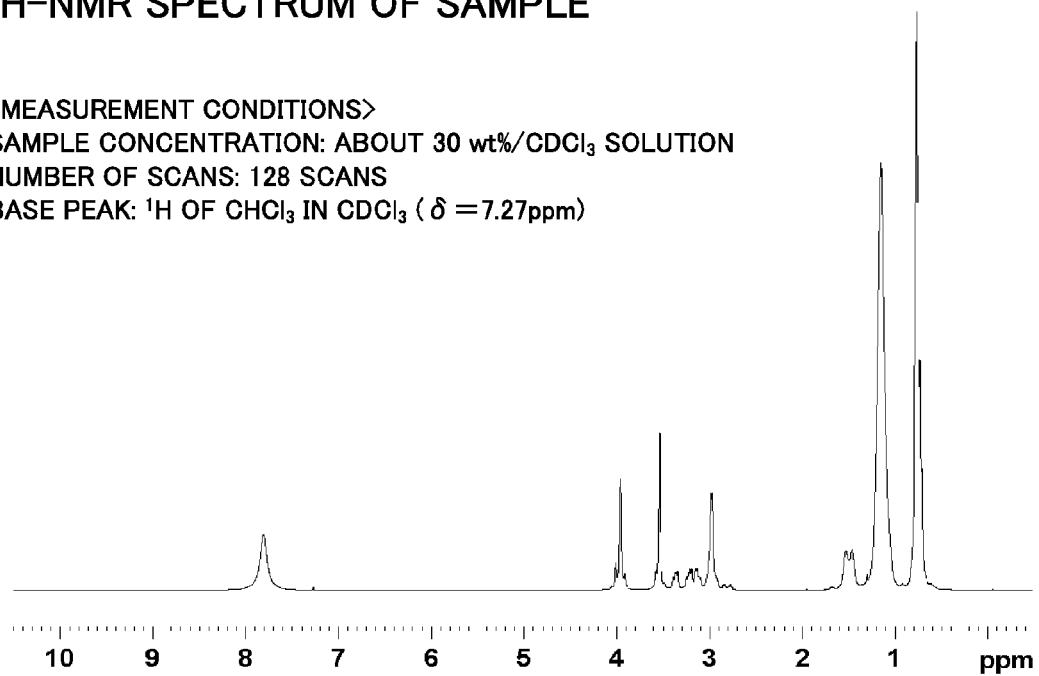
FIG. 1 is a drawing showing the $^1$H-NMR spectrum of a glycine amide derivative synthesized in Example.

Specific embodiments of the present invention will be now described in detail. It is noted, however, that the present invention is not limited to the following embodiments, and can be properly changed within the scope of the object of the present invention and carried out.

<Zirconium Extraction Agent>

The zirconium extraction agent of the present invention comprises an amide derivative represented by the following general formula (I).

[Chem. 3]

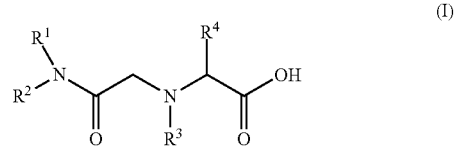

In the formula, $R^1$ and $R^2$ each represent the same or different alkyl group. The alkyl group may be a straight chain or a branched chain, and the alkyl group is preferably a branched chain because of excellent solubility in organic solvents. Besides, it is more preferred that the alkyl group be a branched chain and furthermore the lengths of $R^1$ and $R^2$ be different from each other because of more excellent solubility in organic solvents.

The number of carbons in the alkyl group is not particularly limited, and is preferably 5 or more and 11 or less and more preferably 7 or more and 9 or less. When the number of carbons is too small, a zirconium extraction agent becomes water-soluble, and the leakage (distribution) of the extraction agent to water can be a problem, which is not preferred. When the number of carbons is too large, the surface active ability of the extraction agent increases and thus an emulsion can be formed, and a third phase other than the aqueous phase and the organic phase can be also formed, which is not preferred.

$R^3$ represents a hydrogen atom or an alkyl group. $R^4$ represents a hydrogen atom or any group other than an amino group which is bound to the α carbon as an amino acid.

In the present invention, lipophilicity is enhanced by introducing an alkyl group into the amide skeleton and the present invention can be used as an extraction agent.

The above amide derivative is preferably any one or more of a glycine amide derivative, a histidine amide derivative, a lysine amide derivative, an aspartic acid amide derivative and a normal-methyl glycine derivative.

When the amide derivative is a glycine amide derivative, the above glycine amide derivative can be synthesized by the following method. First, a 2-halogenated acetyl halide is added to an alkyl amine having a structure represented by $NHR^1R^2$ ($R^1$ and $R^2$ are the same as the above substituents $R^1$ and $R^2$) and the hydrogen atom of the amine is substituted with a 2-halogenated acetyl by a nucleophilic substitution reaction to obtain a 2-halogenated (N,N-di)alkylacetamide.

Next, the above 2-halogenated (N,N-di)alkylacetamide is added to a glycine or N-alkyl glycine derivative, and one hydrogen atom of the glycine or N-alkyl glycine derivative is substituted with a (N,N-di)alkylacetamide group by a nucleophilic substitution reaction. With the two-step reaction, a glycine alkyl amide derivative can be synthesized.

It is noted that by replacing glycine with histidine, lysine or aspartic acid, a histidine amide derivative, a lysine amide derivative or an aspartic acid amide derivative can be synthesized, and it is thought that the extraction behaviors of lysine and aspartic acid derivatives are within the range of the results obtained by using a glycine derivative and a histidine amide derivative from the stability constants of complexes of e.g. manganese and cobalt targets.

When a compound represented by the general formula (I) is a histidine amide derivative, the histidine amide derivative is represented by the following general formula (II).

[Chem. 4]

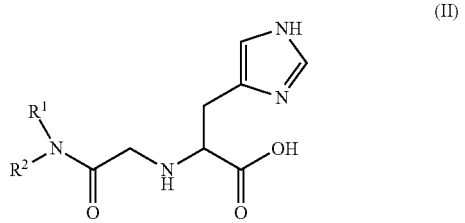

(II)

When the compound represented by the general formula (I) above is a lysine amide derivative, the lysine amide derivative is represented by the following general formula (III).

[Chem. 5]

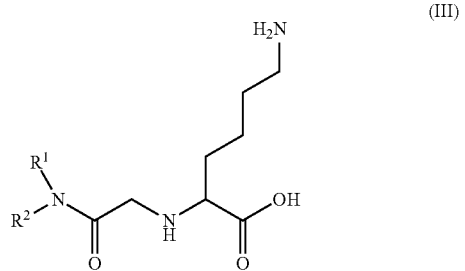

(III)

When the compound represented by the general formula (I) above is an aspartic acid amide derivative, the aspartic acid amide derivative is represented by the following general formula (IV).

[Chem. 6]

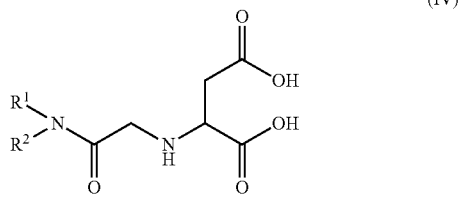

(IV)

<Method for Selectively Extracting Zirconium>

To extract zirconium ions using an extraction agent synthesized by the above method and separate zirconium from scandium, with an adjusted acidic solution containing zirconium ions and scandium ions, the acidic solution is added to an organic solution of the above extraction agent, and mixed. Therefore, zirconium ions can be selectively extracted into the organic phase. When efficiently extracting zirconium from an acidic solution containing zirconium, as long as the extraction agent is the above amino derivative, any compound can be used.

The zirconium extraction agent of the present invention has excellent extraction ability from a strongly acidic solution. Because of this, zirconium can be extracted in the low pH range, in which scandium, titanium, lanthanum, yttrium etc. cannot be extracted. A solution obtained by acid dissolution of a raw material containing zirconium and scandium can be directly subjected to extraction.

The organic solvent can be any solvent in which an extraction agent and metal extraction species are dissolved, and examples thereof include chlorine solvents such as chloroform and dichloromethane, aromatic hydrocarbons such as benzene, toluene and xylene, aliphatic hydrocarbons such as hexane, and the like. These organic solvents may be used alone or two or more solvents may be used in combination. Alcohols such as 1-octanol may be mixed.

The concentration of the extraction agent can be suitably set depending on the concentrations of zirconium and scandium. In addition, because the time to reach equilibrium varies depending on the concentrations of zirconium and scandium and furthermore on the amount of extraction agent to be added, the stirring time and extraction temperature may be suitably set depending on the conditions of the acidic solution of zirconium ions and scandium ions and the organic solution of the extraction agent.

The extraction agent can extract zirconium even in the strongly acidic range, about pH 0.2, in which other metal components cannot be extracted. The organic solvent after extracting several kinds of ions such as zirconium ions is separated, and a back extraction starting solution adjusted to a pH lower than that of the above acidic aqueous solution (e.g. an acid solution with a pH of about 0.2) is added thereto, and the obtained mixture is stirred, thereby retaining zirconium ions in the organic solvent and back-extracting e.g. scandium, titanium, yttrium and lanthanum other than zirconium into the acid solution. Furthermore, by back-extracting zirconium ions from the organic solvent, zirconium ions can be recovered into the aqueous solution. For example, an aqueous solution obtained by diluting nitric acid, hydrochloric acid or sulfuric acid is appropriately used as the back extraction solution. In addition, zirconium ions can be concentrated by suitably changing the ratio of the organic phase and the aqueous phase.

In addition, yttrium, lanthanum etc. are separated by the contact of an acid adjusted to a pH range, about pH 0.8 to 1.5, preferably about 1.0, in which zirconium and scandium are extracted and yttrium and lanthanum are not extracted to increase the proportions of zirconium and scandium, and scandium can be then concentrated and separated from zirconium.

It should be noted that zirconium can be separated and recovered from an extraction agent, for example, by resolving the extraction agent which has extracted zirconium until reaching the limit of its extraction ability by a method such as incineration.

The mechanism in which the extraction agent of the present invention has extraction behaviors different from those of conventional extraction agents is not known exactly, but it is thought that the effects which conventional extraction agents have not had are obtained due to the structural features of the extraction agent of the present invention.

EXAMPLES

The present invention will be now described in more detail by way of examples thereof. It is noted, however, that the present invention is not limited to these descriptions.

Example

As an example of amide derivatives forming an extraction agent, a glycine amide derivative represented by the following general formula (I) was synthesized, that is, N—[N,N-bis(2-ethylhexyl)aminocarbonylmethyl]glycine (or also referred to as N,N-di(2-ethylhexyl)acetamide-2-glycine, hereinafter referred to as "D2EHAG") into which two 2-ethylhexyl groups were introduced.

D2EHAG was synthesized as follows. First, as shown in the following reaction formula (II), 23.1 g (0.1 mol) of commercially available di(2-ethylhexyl)amine and 10.1 g (0.1 mol) of triethylamine were taken and chloroform was added thereto and dissolved. Next, 13.5 g (0.12 mol) of 2-chloroacetyl chloride was added dropwise thereto and the obtained mixture was washed once with 1 mol/l hydrochloric acid and then washed with ion exchanged water, and the chloroform phase was separated.

Next, anhydrous sodium sulfate was added thereto in an appropriate amount (approximately 10 to 20 g) for dehydration, followed by filtration to obtain 29.1 g of yellow liquid. The structure of this yellow liquid (reaction product) was identified using a nuclear magnetic resonance analyzer (NMR) and the above yellow liquid was confirmed to have the structure of 2-chloro-N,N-di(2-ethylhexyl)acetamide (hereinafter, referred to as "CDEHAA"). It is noted that the yield of CDEHAA was 90% with respect to di(2-ethylhexyl) amine, which is a raw material.

[Chem. 7]

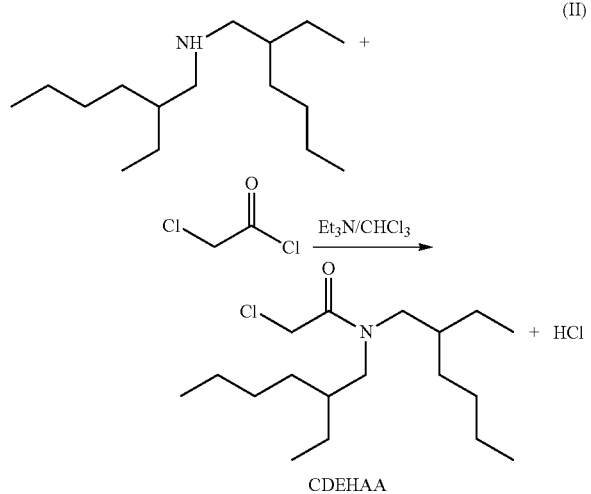

CDEHAA

Next, as shown in the following reaction formula (III), 8.0 g (0.2 mol) of sodium hydroxide was dissolved by adding methanol, and 15.01 g (0.2 mol) of glycine were also added thereto. While stirring the obtained solution, 12.72 g (0.04 mol) of the above CDEHAA were slowly added dropwise thereto and stirred. After completion of stirring, the solvent in the reaction liquid was distilled off and the residue was dissolved by adding chloroform. This solution was acidified by adding 1 mol/l sulfuric acid and then washed with ion exchanged water, and the chloroform phase was separated.

Figure 2:
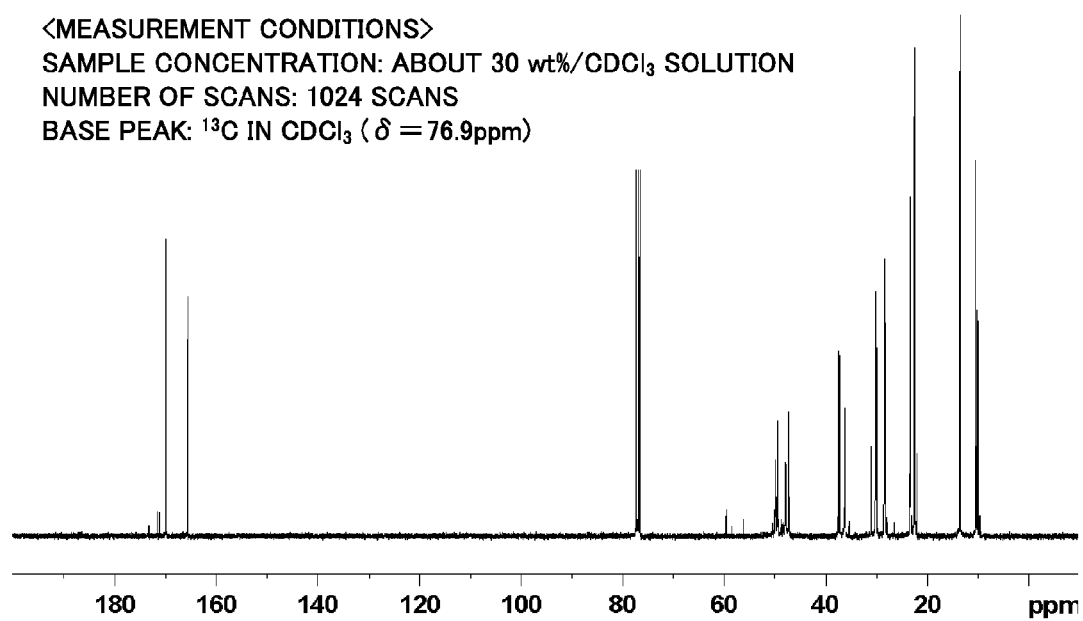
FIG. 2 is a drawing showing the $^{13}$C-NMR spectrum of a glycine amide derivative synthesized in Example.

Anhydrous magnesium sulfate was added to this chloroform phase in an appropriate amount for dehydration, followed by filtration. The solvent was removed under reduced pressure again to obtain 12.5 g of yellow paste. The yield was 87% based on the amount of the above CDEHAA. The structure of the yellow paste was identified by NMR and elemental analysis and the yellow paste was confirmed to have the structure of D2EHAG as shown in FIG. 1 and FIG. 2. The zirconium extraction agent in Example 1 was obtained by the above steps.

[Chem. 8]

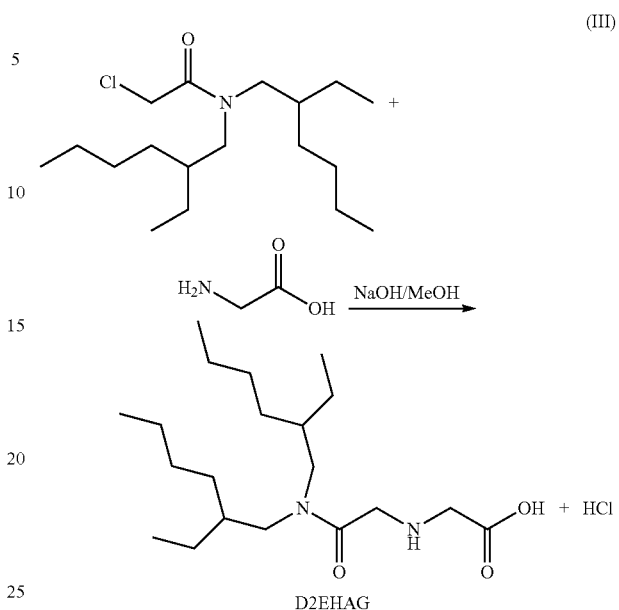

D2EHAG

<Extraction of Zirconium>

Zirconium was extracted using the extraction agent according to Example (D2EHAG).

As an original liquid, several kinds of hydrochloric acid solution containing zirconium, and scandium, titanium, yttrium and lanthanum at a concentration of $1 \times 10^{-4}$ mol/l each and adjusted to a pH of 0.2 to 4.1, and a normal-dodecane solution with the same volume as above comprising a zirconium extraction agent at a concentration of 0.01 mol/l were added to test tubes. The test tubes were put into a thermostatic chamber at 25° C. and shaken for 24 hours. At this time, the pH of hydrochloric acid solutions was adjusted using hydrochloric acid with a concentration of 0.1 mol/l and a solution of sodium hydroxide with a concentration of 1 mol/l.

Figure 3:
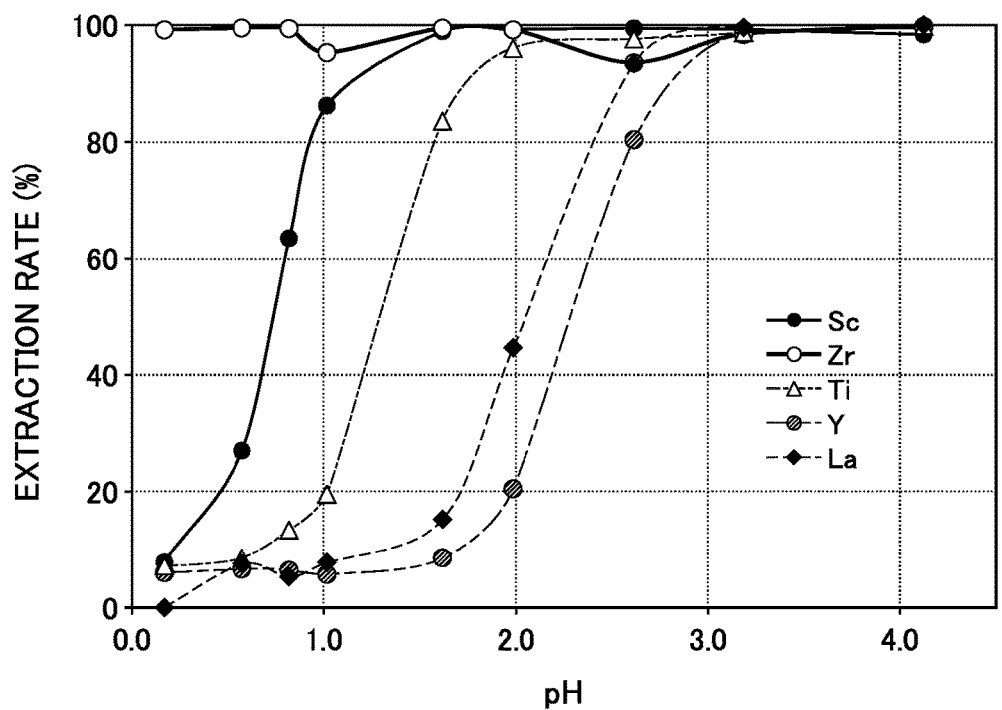
FIG. 3 is a graph showing a relationship between the pH of original liquids and the extraction rates of metals when using an amide derivative synthesized in Example as an extraction agent.

After shaking, the aqueous phase was separated and the concentration of zirconium, and the concentration of scandium, and the concentration of titanium, the concentration of yttrium, and the concentration of lanthanum were measured using an inductively coupled plasma-atomic emission spectrophotometer (ICP-AES). In addition, the organic phase was subjected to back extraction using 1 mol/l hydrochloric acid. The concentration of zirconium, and the concentration of scandium, and the concentration of titanium, the concentration of yttrium, and the concentration of lanthanum in the back extraction phase were measured using ICP-AES. Using these measurement results, the extraction rates of zirconium, scandium, titanium, lanthanum and yttrium were each defined by (1-Concentration after extraction)/(Concentration before extraction)×100 and found. The results are shown in FIG. 3 and Table 1. In FIG. 3, the abscissa is the pH after the extraction of a hydrochloric acid solution and the ordinate is the extraction rates (unit: %) of zirconium, scandium, titanium, yttrium and lanthanum.

TABLE 1

Relationship between pH of original liquids and extraction rates of metals when using amide derivative synthesized in Example as extraction agent

| pH of original liquid | Sc | Zr | Ti | Y | La |
|---|---|---|---|---|---|
| 0.2 | 8 | 99 | 7 | 6 | 0 |
| 0.6 | 27 | 100 | 9 | 7 | 8 |
| 0.8 | 64 | 99 | 14 | 7 | 5 |
| 1.0 | 86 | 95 | 20 | 6 | 8 |
| 1.6 | 99 | 100 | 84 | 9 | 15 |
| 2.0 | 99 | 99 | 96 | 21 | 45 |
| 2.6 | 99 | 94 | 98 | 80 | 94 |
| 3.2 | 99 | 99 | 99 | 99 | 100 |
| 4.1 | 99 | 100 | 100 | 100 | 100 |

(Unit: %)

Even when the pH is in the strongly acidic range, about 0.2, the extraction rate of zirconium is almost 100% using the zirconium extraction agent in Example. On the other hand, scandium is extracted only at an extraction rate of about 10% at around pH 0.2, but extracted at an extraction rate of 80% or more at pH 1.0. Furthermore, it is found that titanium, yttrium and lanthanum are extracted only at an extraction rate of about 10 to 20% at around pH 1.0, and extracted only in a range of pH 1.5 or higher.

As described above, it was verified that using the extraction agent of the present invention, zirconium could be separated from scandium, titanium, yttrium and lanthanum and recovered by adjusting the pH.

The invention claimed is:

1. A method for extracting zirconium, wherein a first acidic solution containing zirconium or containing zirconium and scandium is subjected to solvent extraction with a zirconium extraction agent consisting of amide derivatives represented by the following general formulas to extract the zirconium from the first acidic solution:

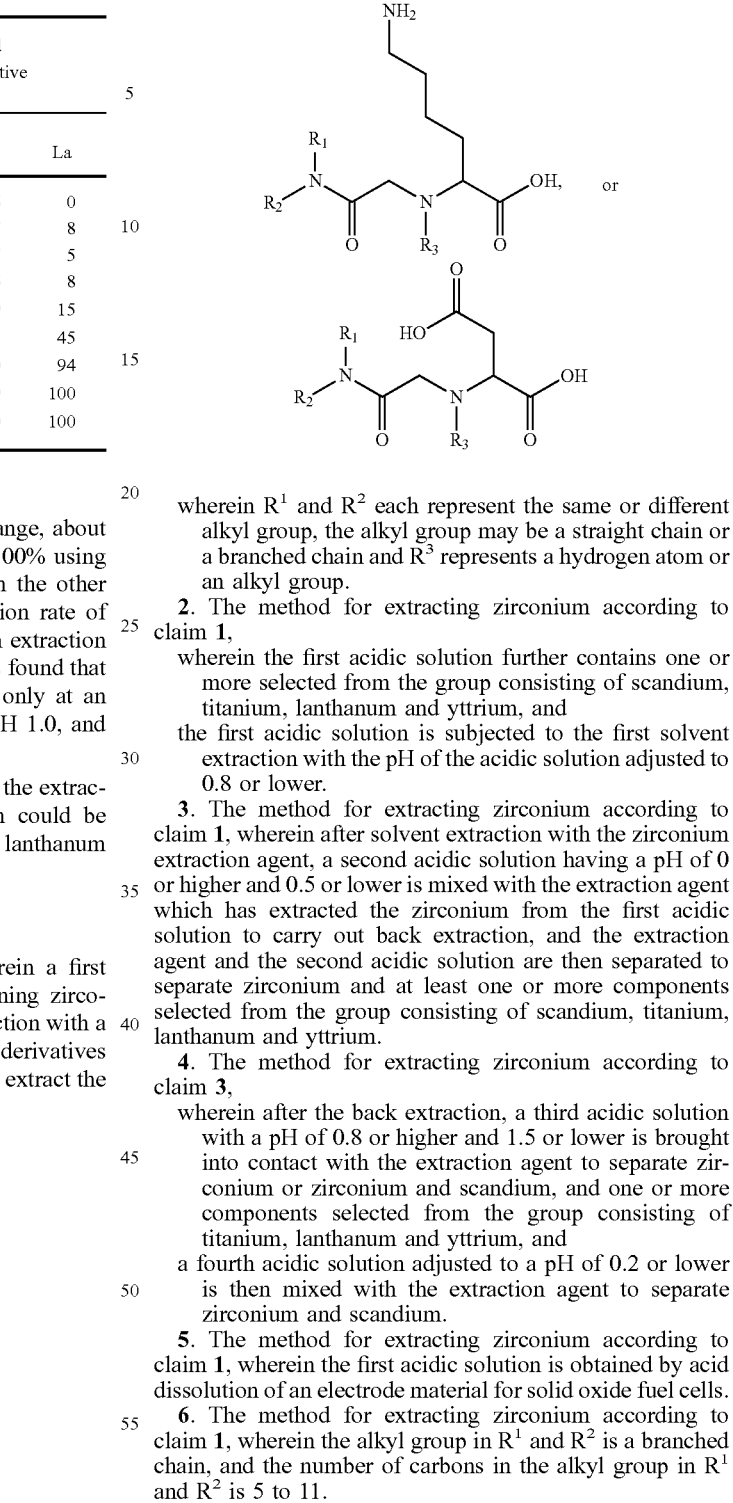

wherein $R^1$ and $R^2$ each represent the same or different alkyl group, the alkyl group may be a straight chain or a branched chain and $R^3$ represents a hydrogen atom or an alkyl group.

2. The method for extracting zirconium according to claim 1,
wherein the first acidic solution further contains one or more selected from the group consisting of scandium, titanium, lanthanum and yttrium, and
the first acidic solution is subjected to the first solvent extraction with the pH of the acidic solution adjusted to 0.8 or lower.

3. The method for extracting zirconium according to claim 1, wherein after solvent extraction with the zirconium extraction agent, a second acidic solution having a pH of 0 or higher and 0.5 or lower is mixed with the extraction agent which has extracted the zirconium from the first acidic solution to carry out back extraction, and the extraction agent and the second acidic solution are then separated to separate zirconium and at least one or more components selected from the group consisting of scandium, titanium, lanthanum and yttrium.

4. The method for extracting zirconium according to claim 3,
wherein after the back extraction, a third acidic solution with a pH of 0.8 or higher and 1.5 or lower is brought into contact with the extraction agent to separate zirconium or zirconium and scandium, and one or more components selected from the group consisting of titanium, lanthanum and yttrium, and
a fourth acidic solution adjusted to a pH of 0.2 or lower is then mixed with the extraction agent to separate zirconium and scandium.

5. The method for extracting zirconium according to claim 1, wherein the first acidic solution is obtained by acid dissolution of an electrode material for solid oxide fuel cells.

6. The method for extracting zirconium according to claim 1, wherein the alkyl group in $R^1$ and $R^2$ is a branched chain, and the number of carbons in the alkyl group in $R^1$ and $R^2$ is 5 to 11.

* * * * *